(12) United States Patent
Rottiers et al.

(10) Patent No.: US 9,017,662 B2
(45) Date of Patent: Apr. 28, 2015

(54) ANTI-TNF ALPHA PRODUCING LACTIC ACID BACTERIA FOR THE TREATMENT OF CHRONIC ENTEROCOLITIS

(75) Inventors: Pieter Rottiers, De Pinte (BE); Klaas Vandenbroucke, Ghent (BE)

(73) Assignee: Actogenix N.V., Zwijnaarde (BE)

( * ) Notice: Subject to any disclaimer, the term of this patent is extended or adjusted under 35 U.S.C. 154(b) by 1721 days.

(21) Appl. No.: 12/065,335

(22) PCT Filed: Aug. 30, 2006

(86) PCT No.: PCT/EP2006/065803
§ 371 (c)(1),
(2), (4) Date: Mar. 3, 2008

(87) PCT Pub. No.: WO2007/025977
PCT Pub. Date: Mar. 8, 2007

(65) Prior Publication Data
US 2008/0274084 A1  Nov. 6, 2008

(30) Foreign Application Priority Data

Aug. 30, 2005 (EP) .................................. 05107909
Dec. 2, 2005 (EP) .................................. 05111654

(51) Int. Cl.
*A01N 63/00* (2006.01)
*C07K 16/24* (2006.01)

(52) U.S. Cl.
CPC ......... *C07K 16/241* (2013.01); *C07K 2317/569* (2013.01)

(58) Field of Classification Search
None
See application file for complete search history.

(56) References Cited

U.S. PATENT DOCUMENTS

| | | | |
|---|---|---|---|
| 5,919,452 A | 7/1999 | Le et al. | |
| 6,746,671 B2 * | 6/2004 | Steidler et al. | 424/93.2 |
| 2006/0034845 A1 | 2/2006 | Silence et al. | |

FOREIGN PATENT DOCUMENTS

| | | |
|---|---|---|
| EP | 1 481 681 | 12/2004 |
| FR | 2 810 337 | 12/2001 |
| WO | WO 94/25591 | 11/1994 |
| WO | WO 97/14806 | 4/1997 |
| WO | WO 00/23471 | 4/2000 |
| WO | WO 2004/041862 | 5/2004 |
| WO | WO 2004/041863 | 5/2004 |

OTHER PUBLICATIONS

Vandenbroucke et al., 4th Annual BMRP Investigator Meeting—Abstract. http://www.broadmedical.org/funding/funded-grants/2004/Abstract-Vandenbroucke, accessed Mar. 18, 2011.*
Lamprecht, et al. "Carrier Systems for the Treatment of Inflammatory Bowel Disease," *Drugs of the Future*, vol. 27, No. 10, pp. 961-971, 2002.
International Search Report dated Apr. 5, 2007.
Kuipers, et al. "Controlled Overproduction of Proteins by Lactic Acid Bacteria," *Trends in Biotechnology*, vol. 15, pp. 135-140, Apr. 1997.
Worledge, et al. "Oral Administration of Avian Tumor Necrosis Factor Antibodies Effectively Treats Experimental Colitis in Rats," *Digestive Diseases and Sciences*,, vol. 45, No. 12, p. 2298-2305, Dec. 2000.
Third party observations submitted in the pending European counterpart application 06778386.0-2107 (EP1948206) dated Jan. 2, 2012.
Caluwaerts et al., "AG013, a mouth rinse formulation of *Lactococcus lactis* secreting human Trefoil Factor 1, provides a safe and efficacious therapeutic tool for treating oral mucositis," *Oral Oncology*, vol. 46, pp. 564-570 (2010).
Limaye et al., "Phase 1b, Multicenter, Single Blinded, Placebo-Controlled, Sequential Dose Escalation Study to Assess the Safety and Tolerability of Topically Applied AG013 in Subjects With Locally Advanced Head and Neck Cancer Receiving Induction Chemotherapy," *Cancer*,119 (24): 4268-4276, (Dec. 15, 2013).

* cited by examiner

*Primary Examiner* — Irene Marx
(74) *Attorney, Agent, or Firm* — Knobbe, Martens, Olson & Bear LLP

(57) ABSTRACT

Treatments for chronic enterocolitis are disclosed. More specifically, methods for administration of pharmaceutical compositions that include anti-TNF-alpha antibody producing lactic acid microorganisms, such as *Lactobacillus* sp. and *Saccharomyces* sp., are disclosed for the treatment of chronic enterocolitis.

2 Claims, 5 Drawing Sheets

ANTI-TNF ALPHA PRODUCING LACTIC ACID BACTERIA FOR THE TREATMENT OF CHRONIC ENTEROCOLITIS

CROSS-REFERENCE TO RELATED APPLICATIONS

This application is the U.S. National Phase under 35 U.S.C. §371 of International Application PCT/EP2006/065803, filed Aug. 30, 2006, which claims priority to EP 05107909.3, filed Aug. 30, 2005 and EP 05111654.9, filed Dec. 2, 2005.

The present invention relates to a novel treatment of chronic enterocolitis. More specifically, the invention relates to the production of a medicament comprising anti-TNFα producing lactic acid bacteria, and the use of this medicament in the treatment of chronic enterocolitis.

Inflammatory bowel disease (IBD) refers to a group of gastrointestinal disorders characterized by a chronic non-specific inflammation of portions of the gastrointestinal tract. The most prominent examples of IBD in humans are ulcerative colitis (UC) and Crohn's disease (CD). The etiology or etiologies of IBD are unclear. IBD diseases appear to result from the unrestrained activation of an inflammatory response in the intestine. This inflammatory cascade is thought to be perpetuated through actions of proinflammatory cytokines and selective activation of lymphocyte subsets. UC and CD are associated with many symptoms and complications, including growth retardation in children, rectal prolaps, blood in stools, wasting, iron deficiency and anemia. UC refers to a chronic, non-specific, inflammatory and ulcerative disease having manifestations primarily in the colonic mucosa. It is frequently characterized by bloody diarrhea, abdominal cramps, blood and mucus in the stoll, malaise, fever, anemia, anorexia, weight loss, leukocytosis, hypoalbuminemia and an elevated erythrocyte sedimentation rate.

Crohn's disease shares many features in common with ulcerative colitis. Crohn's disease is distinguishable in that lesions tend to be sharply demarcated from adjacent normal bowel, in contrast to the lesions of ulcerative colitis which are fairly diffuse. Additionally, Crohn's disease predominantly afflicts the ileum (ileitis) and the ileum and colon (ileocolitis). In some cases, the colon alone is diseased (granulomatous colitis) and sometimes the entire small bowel is involved.

Colon cancer is a known complication of chronic IBD. It is increasingly common in those patients who have IBD for many years. The risk for cancer begins to rise significantly after eight to ten years of IBD, making a fast and efficient treatment of IBD even more important.

The most commonly used medication to treat IBD includes anti-inflammatory drugs such as corticosteroids and sulicilates such as sulphasalazine and its derivatives. For people that not respond to these drugs, immunosuppressive drugs such as cyclosporine A, mercaptopurin and azathropine are used. However, these medicaments all have serious side effects. A recent, successful development in the treatment of IBD consists in the use of compounds, blocking the working of TNF or its receptor. In that respect is the use of TNF antibodies one of the most promising new therapies. Tumor necrosis factor α (TNFα) is a cytokine produced by numerous cell types, including monocytes and macrophages, that was originally identified based on its capacity to induce the necrosis of certain mouse tumors (see e.g., Old, L. (1985) Science 230:630-632). TNFα has been implicated in the pathophysiology of a variety of other human diseases and disorders, including sepsis, infections, autoimmune diseases, transplant rejection and graft-versus-host disease (see e.g. Moeller, A. et al. (1990) Cytokine 2:162-169; U.S. Pat. No. 5,231,024 to Moeller et al; European Patent Publication No. 260 610 (B1) by Moeller, A. et al.; Vasilli. P. (1992) Annu. Rev. Immunol. 10:411-452; Tracey, K. J. and Cerami, A. (1994) Annu. Rev. Med. 45:491-503). Because of the harmful role of human TNFα (hTNFα) in a variety of human disorders, therapeutic strategies have been designed to inhibit or counteract hTNFα activity. In particular, antibodies that bind to, and neutralize, hTNFα have been sought as a means to inhibit hTNFα activity.

Several antibody preparations have been tested for the treatment of IBD. Although polyclonal antibodies have been tested in phase II clinical tests, monoclonal antibodies are clearly preferred. Infliximab is a chimeric human-mouse monoclonal antibody of the IgG1K subclass, which specifically targets and irreversibly binds to TNFα on cell membranes and in blood. Single intravenous doses, ranging from 5 to 20 mg/kg of the antibody infliximab resulted in a drastic clinical improvement in active Crohn's disease; it has been launched on the market to treat Crohn's disease in 1998.

To solve possible problems linked to chimeric antibodies, the human monoclonal TNFα adalimumab was developed, which is currently tested in phase III clinical trials for the treatment of Crohn's. To improve the half-life time of the antibody in patients, Celltech developed Certolizumab pegol, which is a humanized monoclonal pegylated anti-TNFα antibody, which is currently also tested in phase III clinical trials for the treatment of Crohn's.

However, in all those cases, the antibodies are applied in a systemic way, mainly by subcutaneous injection. Systemic administration of anti TNF-α antibody may result in rather serious unwanted effects, including headache, abscess, upper respiratory tract infection and fatigue.

The unwanted effects associated with systemic delivery could be solved by local delivery on the place of the inflammation. A promising system for delivery of biological active compounds in the intestine has been disclosed in WO97/14806 whereby non-invasive gram positive bacteria such as lactic acid bacteria are used to deliver biological active compounds in the gut. WO00/23471 discloses that this system can be used to deliver IL-10 to the ileum, whereby this strain can be used to treat IBD. WO01/98461 discloses an alternative method for intestinal delivery using yeast. However, although the delivery of biologically active compounds is described, these documents do not teach the delivery of antibodies in the intestine. The in situ production of active antibodies in the intestine is far from straightforward, as both folding and secretion of the antibody are critical. Especially, the stabilization of the structure by sulfur bridges may cause problems for the production of antibodies in bacteria or yeasts. Moreover, whereas cytokines like IL-10 fulfill a catalytic function, TNF antibodies need to be produced in a sufficient amount to inactivate the endogenous produced TNF. Surprisingly, we found that the local delivery of anti TNF-α antibody by a genetically engineered micro-organism can be used in an efficient way to treat IBD.

A first aspect of the invention is the use of a genetically modified micro-organism, producing an anti TNF-α antibody, for the preparation of a medicament to treat IBD. The term antibody, as used here, includes, but is not limited to conventional antibodies, chimeric antibodies, single chain antibodies, bifunctional antibodies, bivalent antibodies, diabodies, and camelid antibodies, including antibody fragments such as VHHs; Preferably said antibody is a camelid antibody fragment (VHH; further called nanobody), even more preferably said antibody is a bivalent anti-TNFα nanobody. Bivalent antibodies have the advantage to inhibit TNF binding to its receptor, in a significantly more efficient fashion than does monovalent (EC50=16 pM and 6.7 nM, respectively). Surprisingly we found that the production of bivalent antibodies in *Lactococcus* is as high or even higher than that of monovalent antibodies.

Preferably, said genetically modified micro-organisms is a lactic acid bacterium or a yeast. Delivery of biologically active polypeptides into the animal body by lactic acid bacteria has been disclosed in WO9714806; intestinal delivery of peptides by yeast has been described in WO0198461. However, none of these documents mention the delivery of antibodies or nanobodies in the intestine. Production, secretion and delivery in vivo of biological active antibodies or nanobodies is far from evident, as a correct folding and secretion of the antibody is required, and sufficient antibody is required to obtain a neutralizing activity.

In one preferred embodiment said genetically modified micro-organism is a *Lactococcus lactis* strain, preferably said genetically a *Lactococcus lactis* ThyA mutant. A specially preferred embodiment is the use of a *Lactococcus lactis* ThyA mutant, whereby the gene encoding the TNF-α antibody has been used to disrupt the THYA gene.

In another preferred embodiment, a yeast is be used to deliver the anti TNF-α antibody. Preferably said yeast is *Saccharomyces cerevisiae*, even more preferably said yeast is *Saccharomyces cerevisiae* subsp. *Boulardii*.

IBD, as used here, includes but is not limited to chronic colitis, ulcerative colitis and Crohn's disease. Preferably, IBD is chronic colitis.

Another aspect of the invention is a pharmaceutical composition for oral administration, comprising at least one genetically modified anti-TNFα VHH producing micro-organism. Preferably, said anti-TNFα VHH is a bivalent antibody. The pharmaceutical composition may be liquid, comprising biological active micro-organisms, or it may be solid, comprising dried micro-organisms that can be reactivated when put in a suitable environment. Micro-organisms may be dried by any system, including freeze drying and spray drying. "Anti-TNFα VHH producing" as used here doesn't imply that the micro-organism is producing the VHH in the pharmaceutical composition, but it means that the micro-organism is viable and can produce the VHH when placed in a suitable environment. Micro-organisms may be coated to facilitate the delivery into the gastrointestinal tract. Such coating are known to the person skilled in that art and was, amongst others, described by Huyghebaert et al. (2005). The pharmaceutical composition may further comprise agents to improve the viability of the micro-organisms, such as, but not limited to trehalose. Preferably, the micro-organisms are selected from the group consisting of lactic acid bacteria and yeasts. One preferred embodiment is a pharmaceutical composition, whereby the VHH producing micro-organism is a *Lactococcus lactis*, preferably a ThyA mutant. Another preferred embodiment is a pharmaceutical composition, whereby the VHH producing micro-organism is a *Lactobacillus* sp. preferably a ThyA mutant. Preferably, said ThyA mutants are obtained by gene disruption, using the VHH encoding construct as insert. Still another preferred embodiment is a pharmaceutical composition whereby the VHH producing micro-organism is *Saccharomyces cerevisiae*, preferably *S. cerevisiae* subspecies *boulardii*.

Another aspect of the invention is a method of preventing, treating and/or alleviating at least one disease or disorder of the gastrointestinal tract, comprising administering to the gastro-intestinal tract an effective amount of an anti-TNFα VHH producing micro-organism. Preferably, said anti-TNFα VHH is a bivalent antibody. The way of administering can be any way known to the person skilled in the art, and includes, but is not limited to oral and rectal administration. Preferably, the way of administering is oral administration. Preferably, said disease or disorder is a disease or disorder characterized by an imbalance in TNFα production, and can be treated by TNFα inactivating compounds such as TNFα antibodies. Even more preferably, said disease is an irritable bowel disease, including but not limited to chronic colitis, ulcerative colitis and Crohn's disease. Most preferably, said disease or disorder is chronic colitis.

Preferably, said genetically modified micro-organisms is a lactic acid bacterium or a yeast. In one preferred embodiment said genetically modified micro-organism is a *Lactococcus lactis* strain, preferably said genetically a *Lactococcus lactis* ThyA mutant. A specially preferred embodiment is a *Lactococcus lactis* ThyA mutant, whereby the gene encoding the TNF-α antibody has been used to disrupt the THYA gene. In another preferred embodiment genetically modified micro-organism is a *Lactobacillus* sp strain, preferably said genetically a *Lactobacillus* ThyA mutant. A specially preferred embodiment is a *Lactobacillus* ThyA mutant, whereby the gene encoding the TNF-α antibody has been used to disrupt the THYA gene.

In another preferred embodiment, a yeast is the anti TNF-α antibody producing micro-organism. Preferably said yeast is *Saccharomyces cerevisiae*, even more preferably said yeast is *Saccharomyces cerevisiae* subsp. *Boulardii*.

EXAMPLES

Material and Methods to the Examples

Bacteria and Plasmids

Figure 1:
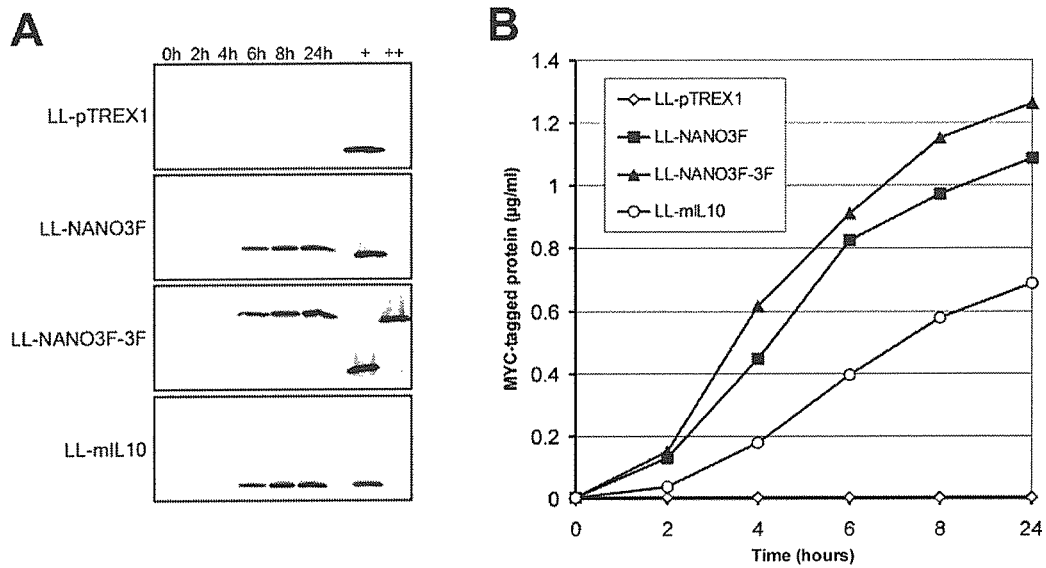
FIG. 1. Time course of heterologous monovalent and bivalent nanobody NANO3F production by GM *L. lactis* (LL-NANO3F and LL-NANO3F-3F). LL-pTREX1: vector control; LL-mIL10: *L. lactis* strain secreting murine interleukin-10. (A) Western blot analysis of proteins secreted from the various strains revealed by anti-Myc Ab. Each lane on the blot represents 250 μL of *L. lactis* culture supernatant obtained after different periods of growth ($2 \times 10^7$ CFU at time zero). *E. coli* purified monovalent NANO3F (+) and bivalent NANO3F-3F (++) were used as positive control. (B) Concentrations of secreted heterologous Myc-tagged proteins in culture supernatants of LL-pTREX1 (◇), LL-NANO3F (■), LL-NANO3F-3F (▲) and LL-mIL10 (○), as determined by ELISA.

The *L. lactis* strain MG1363 was used throughout this study. Bacteria were cultured in GM17 medium, i.e. M17 (Difco Laboratories, Detroit, Mich.) supplemented with 0.5% glucose. Stock suspensions of all strains were stored at −20° C. in 50% glycerol in GM17. For intragastric inoculations, stock suspensions were diluted 200-fold in fresh GM17 and incubated at 30° C. They reached a saturation density of 2×10$^9$ colony-forming units (CFU) per mL within 16 hours. Bacteria were harvested by centrifugation and concentrated 10-fold in BM9 medium. (Schotte, Steidler et al. 2000). For treatment, each mouse received 100 µL of this suspension daily by intragastric catheter.

Identification and Formatting of an Anti-MurineTNF Nanobody

The generation of anti-murine TNF nanobody was essentially carried out as described in WO2004041862. After immunizing llamas with mTNF, subsequent cloning of the VHH repertoire and panning, Nanobody NANO3F (MW-15 kDa) was isolated. The murine TNF specific Nanobody was converted into a bivalent format (coded NANO3F-3F, MW-30 kDa) using the 12 aminoterminal residues of the llama IgG2a upper hinge sequence as a spacer. The cDNA of the NANO3F and NANO3F-3F, extended at their 3' ends with the sequence encoding the HisG and Myc-tag, were fused to the Usp45 secretion signal (van Asseldonk, Rutten et al. 1990) downstream of the lactococcal P1 promotor (Waterfield, Le Page et al. 1995) and expressed in MG1363 (details of plasmid construction can be obtained from the authors). MG1363 strains transformed with plasmids carrying the NANO3F or NANO3F-3F coding sequence were designated LL-NANO3F and LL-NANO3F-3F respectively. LL-pTREX1, which is MG1363 containing the empty vector pTREX1, served as control.

Quantification of Nanobody in *L. lactis* Medium.

Myc-tagged LL-NANO3F and LL-NANO3F-3F were quantified by direct adsorption of crude *L. lactis* supernatants to ELISA plates (Maxisorp F96, Nunc, Rochester, N.Y.) and subsequent detection with a specific mouse mAb against the Myc epitope (Sigma, St. Louis, Mo.).

For quantification of 3F-3F nanobodies secreted in vivo in colon tissue, the entire colon was homogenized in PBS containing 1% BSA and sonicated. The 3F-3F nanobodies were measured in the colon supernatant with the nanobody quantification protocol.

Measurement of Anti-Nanobody Antibody Levels in Mouse Serum.

Mice were injected intraperitoneally with 100 µg Nanobody, or intragastically with LL-NANO3F-3F, daily over a 14 day-period and were subsequently bled. We coated Nanobody at a concentration of 10 µg/ml in microtiterplates (NUNC Maxisorb) overnight at 4° C. The plate was washed 5 times with PBS-Tween and blocked for 2 hours at RT with PBS-1% casein. The samples were applied at a 1/50 dilution in PBS for 2 hours at RT. The plate was washed 5 times and detection was performed by incubation with rabbit-polyclonal-anti-mouse-immunoglobulin-HRP (DAKO, 3,000-fold diluted) for one hour at RT, and after washing plates were stained with ABTS/H202. The OD405 nm was measured.

Anti-Soluble and Membrane-bound TNF Bioassay

The inhibitory effect of the NANO3F and NANO3F-3F nanobodies on soluble mTNF (20 IU/mL) was measured in a 16 hour cytotoxicity assay using the mouse fibroblast WEHI 164 cl 13 cells in the presence of 1 µg/ml actinomycin D, as described. (Espevik and Nissen-Meyer 1986)

The effect of NANO3F and NANO3F-3F to counteract the cytotoxic effect of membrane-bound TNF was determined on the WEHI 164 cl 13 cells after adding L929 cells, expressing uncleavable, membrane-bound TNF to the cell culture (Decoster et al. 1998).

Stimulation of Macrophages with LPS

To measure the effect of NANO3F-3F on the induction of proinflammatory cytokines by LPS, MF4/4 macrophages (Desmedt et al. 1998) were incubated with NANO3F-3F (100 µg/ml). After 1 hour cells were extensively washed (3×) in a sufficient volume of PBS to completely remove all nanobody present in solution. The cells were resuspended and incubated in the presence or absence of LPS for 4 hours. The cells were washed (1×) in PBS and after 4 hours of incubation, the supernatans and cells were separated by centrifugation. To measure the soluble TNF release, the WEHI 164 cl 13 cells bioassay was used.

Animals 11-week old female BALB/c mice were obtained form Charles River Laboratories (Sulzfeld, Germany). They were housed under SPF conditions. IL-10 knockout mice (129Sv/Ev IL-10$^{-/-}$) (Kuhn, Lohler et al. 1993) were housed and bred under SPF conditions. The IL-10$^{-/-}$ mice were used at 20 weeks of age, at which time chronic colitis had fully developed. All mice were fed standard laboratory feed and tap water ad libitum. The animal studies were approved by the Ethics Committee of the Department for Molecular Biomedical Research, Ghent University (File No. 04/02).

Induction of Chronic Colitis by DSS

Mice weighing approximately 21 g were induced to chronic colitis by four cycles of administration of 5% (w/v) DSS (40 kDa, Applichem, Darmstadt, Germany) in the drinking water, alternating with 10-day periods of recovery with normal drinking water. (Okayasu, Hatakeyama et al. 1990; Kojouharoff, Hans et al. 1997) Treatment was arbitrarily initiated at day 21 after the fourth cycle of DSS.

Myeloperoxidase (MPO) Assay

MPO activity in the middle colon tissue was measured as described (Bradley, Priebat et al. 1982). Pure human MPO was used as a standard (Calbiochem, San Diego, Calif.). Data are expressed as µg MPO/mm$^2$ colon tissue.

Histological Analysis

For histological analysis, the colon was removed, cleaned and opened longitudinally. A segment of 1 cm was taken from the middle part of the colon, embedded in paraffin and sectioned longitudinally. Three sections of 4 µm were cut at 200 µm intervals and stained with hematoxylin/eosin. Colon sections were numbered randomly and interpreted semiquantitatively in a blinded manner by a pathologist. The histological score is the sum of the epithelial damage and lymphoid infiltration, each ranging from 0 to 4 as described (Kojouharoff, Hans et al. 1997).

Statistical Analysis

All data are expressed as mean±SEM Parametric data were analyzed with a 1-way analysis of variance followed by a Dunnett multiple comparisons posttest. Nonparametric data (scoring) were analyzed with a Mann-Whitney test.

Example 1

Anti-TNF-α VHH Production by *L. lactis* In Vitro

*L. lactis* was transformed with the plasmids encoding NANO3F and NANO3F-3F. The production of the antibodies was checked by Western blot and ELISA, using a strain transformed with the empty plasmid pTREX and an IL10 producing strain as reference. The results are shown in FIG. 1. NANO3F-3F is produced by *L. lactis* in similar or higher amounts than NANO3F. The amount produced is significantly higher than for IL10.

Example 2

LL-NANO3F-3F is Bioactive and Inhibits Both Soluble and Membrane Bound TNF-α

Figure 2A:
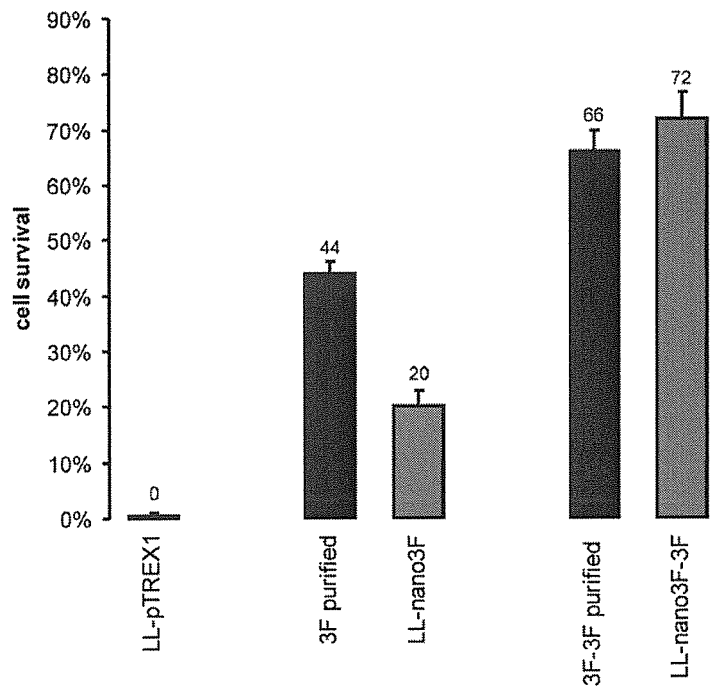
FIG. 2. *L. lactis* secreted or *E. coli* purified monovalent and bivalent nanobody NANO3F are able to efficiently neutralize soluble and membrane bound TNF. (A) soluble TNF (20 IU/ml) was neutralized by NANO3F and NANO3F-3F in a 16 hour cytotoxicity assay using the WEHI 164 cl 13 cells in the presence of 1 μg/ml actinomycin D. (B) *L. lactis* secreted and *E. coli* purified nanobodies NANO3F and NANO3F-3F were able to inhibit the cytotoxic effects of L929 expressing uncleavable membrane-bound TNF. The gray bars represent wells where purified NANO3F or NANO3F-3F was added (total concentration of 250 ng/mL). The black bars represent wells where 50 μL of filtered (0.22 μm) lactococcal supernatant was added. The final concentration of LL-NANO3F and LL-NANO3F-3F was 250 ng/ml in each setting.

The inhibitory effect of the NANO3F and NANO3F-3F nanobodies, produced by *L. lactis* on soluble mTNF was measured in a cytotoxicity assay using the mouse fibroblast WEHI 164 cl 13 cells as described by Espevik and Nissen-Meyer (1986). *E. coli* produced NANO3F and NANO3F-3F was used as a positive reference. Both the purified nonobodies as well as the nanobodies produced by *L. lactis* can neutralize the soluble TNF. (FIG. 2A)

Figure 2B:
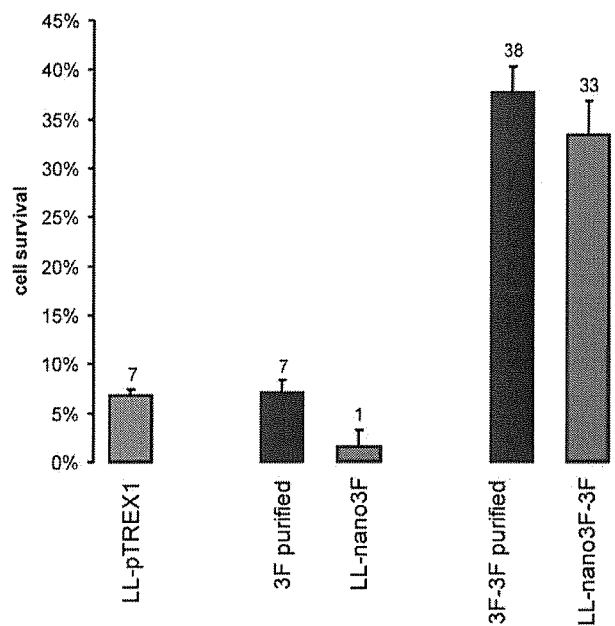

The effect of NANO3F and NANO3F-3F to counteract the cytotoxic effect of membrane-bound TNF was determined on the WEHI 164 cl 13 cells after adding L929 cells, expressing uncleavable, membrane-bound TNF to the cell culture (Decoster et al. 1998). The effect of NANO3F is less pronounced, both with the purified form and the *L. lactis* produced form, but the effect of the NANO3F-3F nanobody is clear in both cases (FIG. 2B)

Example 3

LL-NANO3F-3F Effect In Vivo on Established DSS Induced Chronic Colitis

Figure 3:
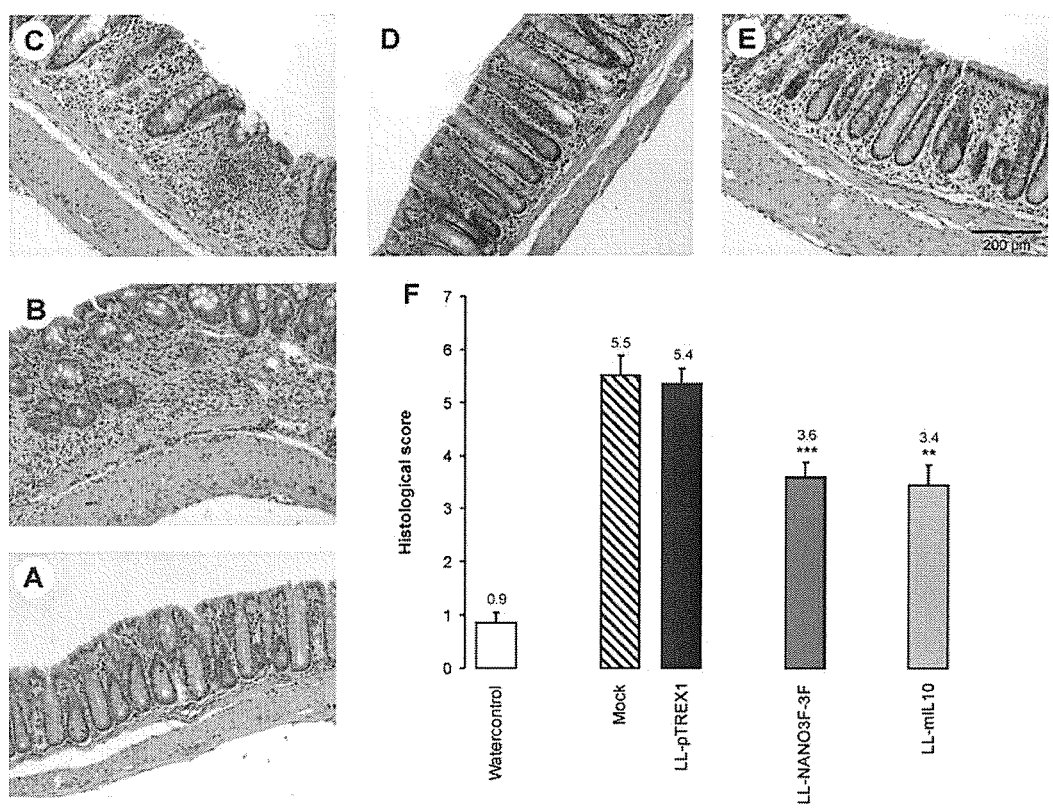
FIG. 3. Analysis of morbidity in chronic DSS colitis. (A-E) Representative histology of the middle colon from healthy control mice (A) and mice with chronic DSS colitis either mock-treated (B) or treated with LL-pTREX1 (C), LL-NANO3F-3F (D) or LL-mIL10 (E). (F) Statistical evaluation of the histological score of the middle colon. Bars represent the mean±SEM. White bar represent the healthy control group. Mice with DSS-induced chronic colitis were either mock-treated (hatched bars) or received LL-pTREX1 (black bar), LL-NANO3F-3F (red bar) or LL-mIL10 (gray bar). * and  represent statistical significant differences in comparison with the mock-treated and the vector control groups of P<0.001 and P<0.01, respectively.

Chronic colitis was induced by DSS as described in materials and methods. Mice were daily treated with 2 10$^9$ colony forming units (cfu) of either LL-pTREX1, LL-NANO3F-3F, or LL-mIL10. A mock treatment, and healthy mice ("water-control") were used as additional control. The effect of the nano3F-3F nanobody delivered by *L. lactis* is comparable to the protection obtained by the in situ produced IL-10 (FIG. 3).

Example 4

LL-NANO3F-3F Effect In Vivo on Established IL-10$^{-/-}$ Enterocolitis

Figure 4:
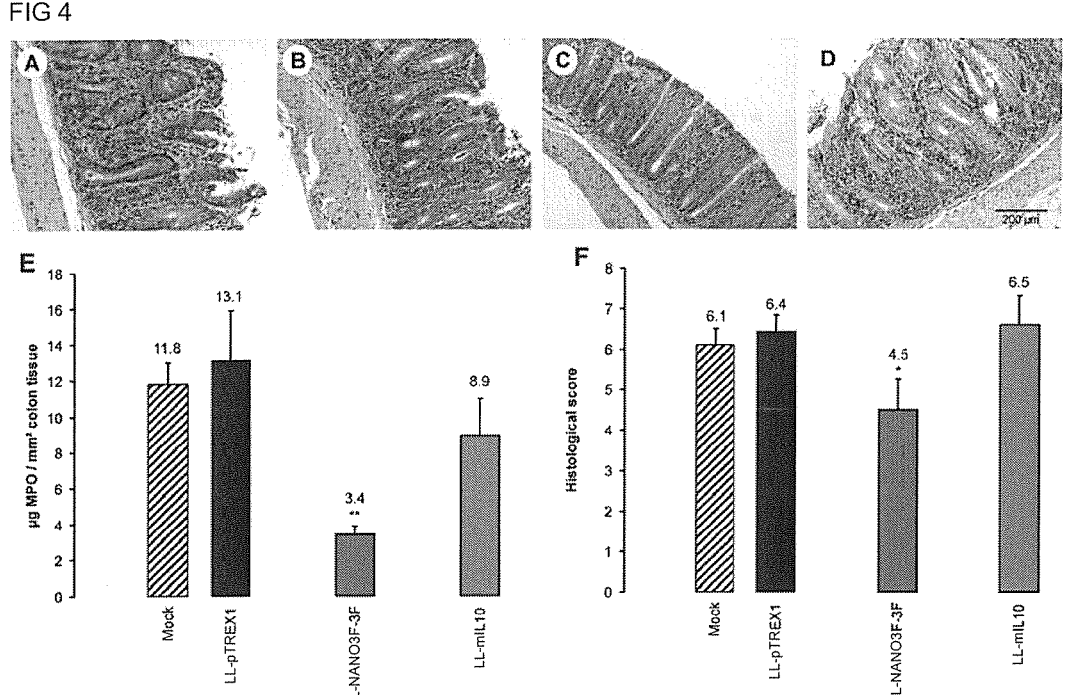
FIG. 4 Analysis of morbidity in 20 weeks old 129Sv/Ev IL-10$^{-/-}$ mice. Each group received daily for 14 days 2×10$^9$ CFU LL-pTREX1 (vector control), LL-NANO3F-3F or LL-mIL10, except the mock treated group. (A-D) Representative histology of the middle colon from IL-10$^{-/-}$ mice which were mock-treated (A) or treated with LL-pTREX1 (B), LL-NANO3F-3F (C) or LL-mIL10 (D) (hematoxylin and eosin staining). Statistical evaluation of the MPO levels per mm$^2$ colon tissue (A) and histological score of the distal colon (B). Bars represent the mean±SEM. Hatched bars represent the 129Sv/Ev IL-10$^{-/-}$ mice that were mock treated, the black bars represent the 129Sv/EV IL-10$^{-/-}$ mice that received the vector control LL-pTREX1, the red bars represent the 129Sv/EV IL-10$^{-/-}$ mice that received LL-NANO3F-3F and the gray bars represent the 129Sv/EV IL-10$^{-/-}$ mice that were treated with LL-mIL10. * and ** represent a statistically significant difference in comparison with the vector control group of P<0.05 and P<0.01, respectively.

To evaluate the protection in IL-10$^{-/-}$ enterocolitis, morbidity in 20 weeks old 129Sv/Ev IL-10$^{-/-}$ treated and untreated mice. Each group received daily for 14 days 2×10$^9$ CFU of either LL-pTREX1 (vector control), LL-NANO3F-3F or LL-mIL10, except the mock treated group. The results are summarized in FIG. 4. Both the myelperoxidase assay as well as the histological score indicate a significant protection in the LL-NANO3F-3F treated mice.

Example 5

Immunogenicity of NANO3F-3F

Figure 5:
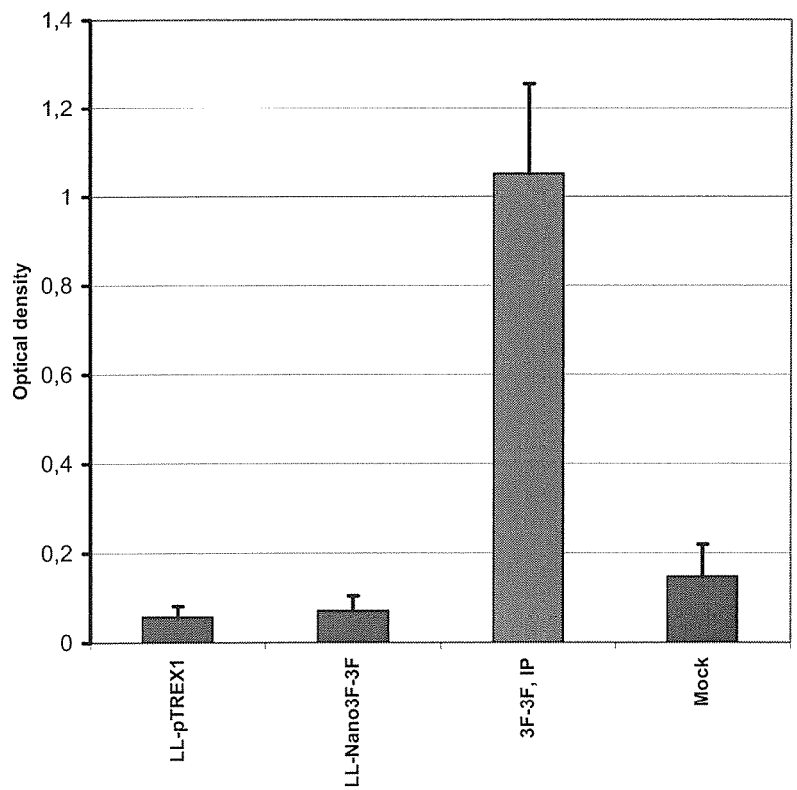
FIG. 5 Presence of nanobody specific antibodies was assessed by ELISA.

To evaluate a possible adverse immunogenic effect of LL-NANO3F-3F, mice were treated intragastrically over a period of 14 days with LL-NANO3F-3F, using intraperitoneal injection of purified nanobody as control. Anti-Nanobody antibody levels were measured in the mouse serum. The results are shown in FIG. 5. While interperitoneal injection of NANO3F-3F is giving a clear immune response, the treatment with LL-NANO3F-3F is not immunogenic and proofs to be safe in that respect.

Example 6

Effect of NANO3F-3F on LPS Induction of Proinflammatory Cytokines

Figure 6:
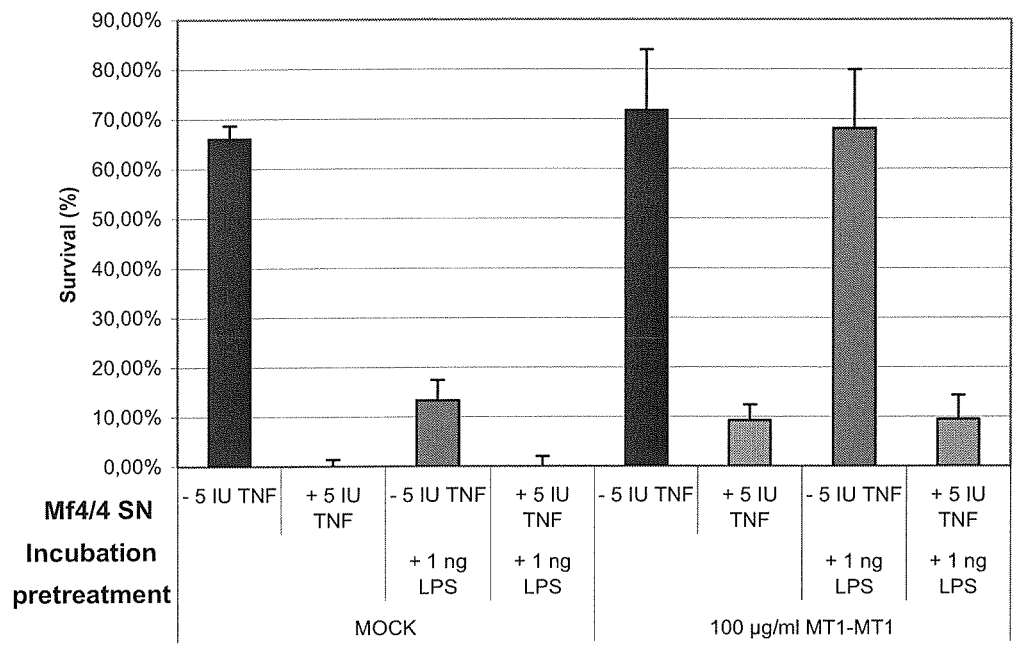
FIG. 6 Pretreatment with NANO3F-3F confers LPS irresponsiveness to Mf4/4 macrophages. WEHI164 cl 13 cells can still be killed with 5 IU TNF FIG. 7 Statistical evaluation of the histological score of the distal colon in mice with chronic DSS colitis. Bars represent the mean±SEM. White bars represent the healthy control group. Mice with DSS-induced chronic colitis received different *L. lactis* cultures for 28 days whereafter the mice were killed and analyzed immediately. The black bar represents the vector control LL-pTREX1 treated group, the hatched bar those that received LL-NANO3F (*L. lactis* secreting monovalent 3F), the gray bar those that received LL-NANO3F-3F (*L. lactis* secreting bivalent 3F-3F-. ** represents a statistical significant difference in comparison with the vector control LL-pTREX1 and the LL-NANO3F treated groups of P<0.01.

To measure the effect of NANO3F-3F on the induction of proinflammatory cytokines by LPS, MF4/4 macrophages (Desmedt et al. 1998) were incubated with NANO3F-3F. The cells were washed and then incubated with LPS. Soluble TNF release was measured using the WEHI 164 cl 13 cell toxicity assay. The results are shown in FIG. 6. Pretreatment of the macrophages with NANO3F-3F nanobody gives a clear protection against LPS induced soluble TNF production.

Example 7

Bivalent Antibodies Perform Surprisingly Better than Monovalent Antibodies

Figure 7:
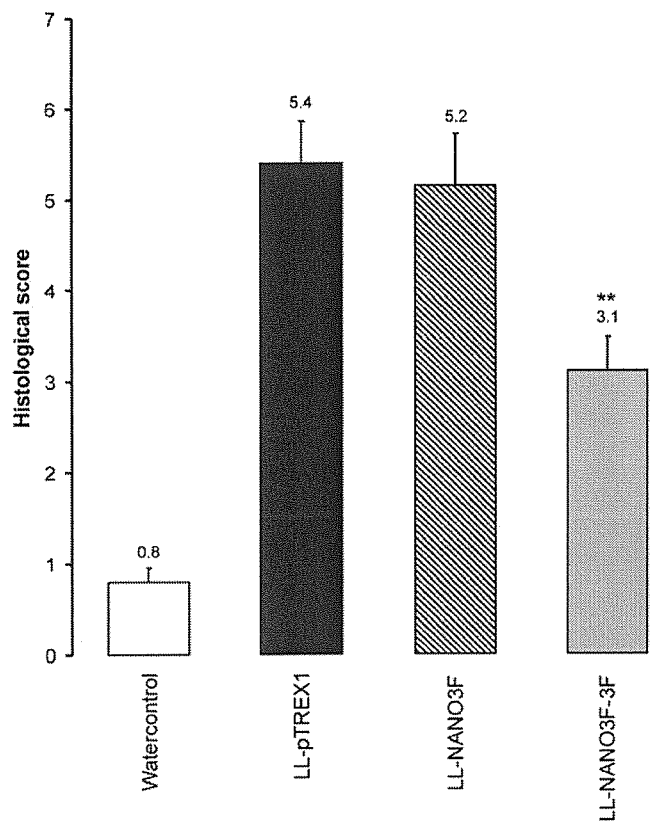
Figure 8:
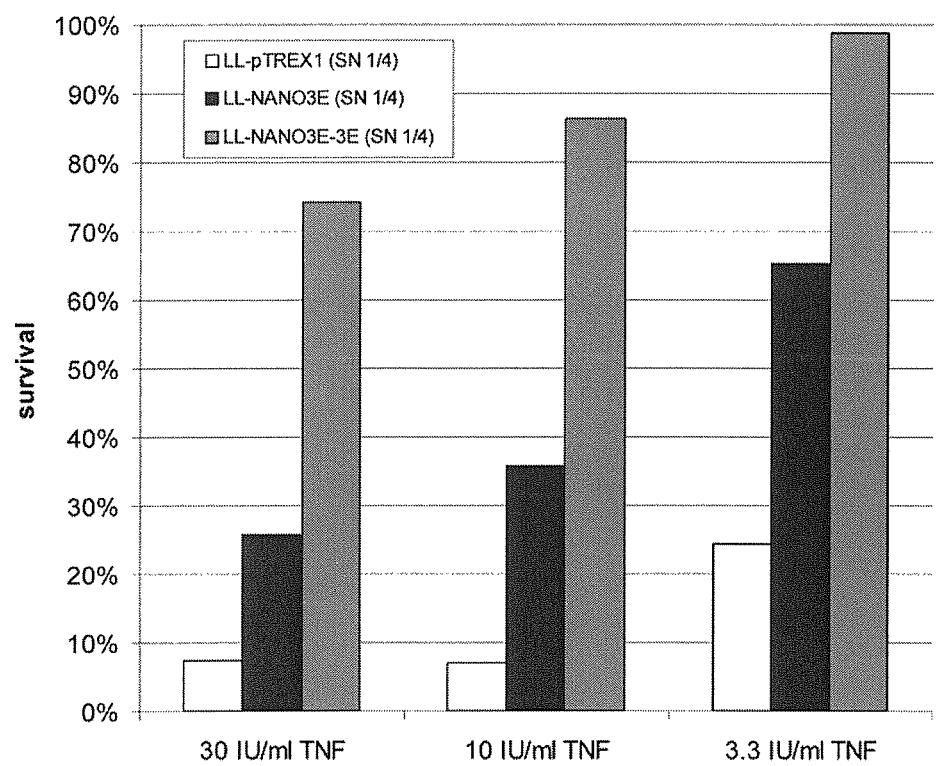
FIG. 8 *L. lactis* secreted monovalent and bivalent Nanobody 3E (anti-human TNF Nanobody) are able to efficiently neutralize soluble human TNF. Soluble human TNF (different concentrations ranging from 30 till 3.3 IU/ml) was neutralized by 3E and 3E-3E in a 16 hour cytotoxicity assay using L929s cells in the presence of 1 µg/ml actinomycin D. Cell survival was calculated relative to healthy cells The white bar represents wells where 50 µL of filtered (0.22 µm) lactococcal supernatant of the vector control LL-pTREX1 was added. Black and gray bars represent wells where 50 µL of filtered (0.22 µm) lactococcal supernatant was added; containing *L. lactis* secreted 3E or 3E-3E, respectively. The final concentration of *L. lactis* secreted 3E or 3E-3E was 250 ng/ml in each setting.

Although bivalent antibodies are larger than monovalent ones, it doesn't affect the production in *Lactococcus*. The production of bivalent antibodies is at least as good if not better than for monovalent antibodies (FIG. 1). However, even more important is the efficacy of the bivalent antibodies. From the in vivo experiments, it is obvious that a monovalent anti-TNF antibody results only in a marginal, non-significant improvement of the histological score, whereas administration of a *L. lactis* secreting bivalent antibodies results in a significant improvement (FIG. 7). Indeed, the neutralizing effect of bivalent antibodies is, for a comparable concentration of protein, more pronounced than that of monovalent antibodies. As long as no complete neutralization is reached, the improvement is more than a factor 2, indicating the effect is not purely due to the double valence of the nanobody (FIG. 8)

REFERENCES

Bradley, P. P., D. A. Priebat, et al. (1982). "Measurement of cutaneous inflammation: estimation of neutrophil content with an enzyme marker." *J Invest Dermatol* 78(3): 206-9.

Espevik, T. and J. Nissen-Meyer (1986). "A highly sensitive cell line, WEHI 164 clone 13, for measuring cytotoxic factor/tumor necrosis factor from human monocytes." *J Immunol Methods* 95(1): 99-105.

Huyghebaert, N., A. Vermeire, S. Neirynck, L. Steidler, E. Remaut, and J. P. Remon. (2005) "Development of an enteric-coated formulation containing freeze-dried, viable recombinant *Lactococcus lactis* for the ileal mucosal delivery of human interleukin-10." *Eur J Pharm Biopharm* 60(3): 349-59

Kojouharoff, G., W. Hans, et al. (1997). "Neutralization of tumour necrosis factor (TNF) but not of IL-1 reduces inflammation in chronic dextran sulphate sodium-induced colitis in mice." *Clin Exp Immunol* 107(2): 353-8.

Kuhn, R., J. Lohler, et al. (1993). "Interleukin-10-deficient mice develop chronic enterocolitis." *Cell* 75(2): 263-74.

Okayasu, I., S. Hatakeyama, et al. (1990). "A novel method in the induction of reliable experimental acute and chronic ulcerative colitis in mice." *Gastroenterolocy* 98(3): 694-702.

Schotte, L., L. Steidler, et al. (2000). "Secretion of biologically active murine interleukin-10 by *Lactococcus lactis*." *Enzyme Microb Technol* 27(10): 761-765.

van Asseldonk, M., G. Rutten, et al. (1990). "Cloning of usp45, a gene encoding a secreted protein from *Lactococcus lactis* subsp. *lactis* MG1363." *Gene* 95(1): 155-60.

Waterfield, N. R., R. W. Le Page, et al. (1995). "The isolation of lactococcal promoters and their use in investigating bacterial luciferase synthesis in *Lactococcus lactis*." *Gene* 165(1): 9-15.

What is claimed is:

1. A method of treating inflammatory bowel disease (IBD) by orally administering a therapeutically effective amount of an anti-TNFα VHH producing *Lactococcus lactis* to an individual in need thereof, wherein said anti-TNFα VHH is a bivalent antibody.

2. The method according to claim 1, wherein said IBD is selected from the group consisting of chronic colitis, Crohn's disease and ulcerative colitis.

\* \* \* \* \*